United States Patent [19]

Buck

[11] Patent Number: Plant 6,183

[45] Date of Patent: May 24, 1988

[54] ROSE PLANT NAMED BUCAROO

[75] Inventor: Griffith J. Buck, Ames, Iowa

[73] Assignee: Iowa State University Research Foundation, Inc., Ames, Iowa

[21] Appl. No.: 843,660

[22] Filed: Mar. 21, 1986

[51] Int. Cl.[4] ..... A01H 5/00

[52] U.S. Cl. ..... Plt./1

[58] Field of Search ..... Plt. 1, 26

*Primary Examiner*—Robert E. Bagwill

*Attorney, Agent, or Firm*—Tilton, Fallon, Lungmus

[57] ABSTRACT

A new variety of shrub rose plant distinguished by its tolerance of low winter temperatures, its resistance to foliar diseases such as Blackspot and Powdery Mildew, and its continuous production of large flowers of light red-purple coloration.

1 Drawing Sheet

BACKGROUND OF THE NEW PLANT

This new rose plant originated as a seedling resulting from a cross of the seed parent Carefree Beauty (Bucbi) (U.S. Plant Pat. No. 4,225) with an unnamed pollen parent obtained by crossing The Yeoman (unpatented) with Country Dancer (unpatented). The new variety was discovered by me at Iowa State University Horticulture Greenhouses, Ames, Iowa, in 1976 and resulted from breeding efforts commenced by me in 1949 at that University. The new plant was selected for propagation because of its continuous and profuse production of large flowers of magenta hue and especially because of its ability to survive winter temperatures in Iowa as low as —35° F. without weather protection and its notable resistance to foliar diseases. Following its discovery, this plant has been asexually reproduced by me by budgrafting at Ames, Iowa, and has been propagated through successive generations to test its retention of the characteristics first observed. Such propagation through successive generations has shown the distinctive characteristics of this new variety hold true from generation to generation and appear to be firmly fixed.

DESCRIPTION OF THE DRAWING

This new variety of rose plant is illustrated by the accompanying photographic drawing which, in full color, shows face and three-quarter side views of opened flowers and several other stages of the bloom from a tight bud to a bud with sepals just cracked. The colors shown are as nearly true as can be reasonably expected to be reproduced by conventional photographic procedures.

DESCRIPTION OF THE NEW PLANT

The following is a description, in detail, of this new variety of hybrid rose plant with color designations according to The R.H.S. Colour Chart (RHSCC) published by The Royal Horticultural Society of London, England, in collaboration with The British Colour Council (BCC), with reference in some cases to the descriptive color designations adopted by the latter.

THE PLANT

Origin: Seedling.

Parentage:

*Seed parent.*—Carefree Beauty (Bucbi), U.S. Plant Pat. No. 4,225.

*Pollen parent.*—An unnamed variety obtained by crossing The Yeoman (unpatented) with Country Dancer (unpatented).

Classification:

*Botanic.*—Rose hybrida.

*Commercial.*—Shrub Rose.

Form: Upright bush.

Height: About 100 to 200 cm. under Iowa's climatic conditions.

Growth: Sturdy and vigorous.

Habit: Free branching erect with strong canes and stems.

Foliage: Abundant quantity.

Leaves:

*Texture.*—Smooth and leathery.

*Color.*—Medium Green 146A (RHSCC) with undersides of lighter Medium Green 147C (RHSCC).

*Leaflets.*—5 to 7 in number and of obovate shape.

*Petioles.*—About 2.1 to 3.0 cm. in length with ribs and veins not prominent.

*Rachis.*—About 4.0 to 5.5 cm. in length.

Thorns and prickles: The plant lacks thorns and spines but it does have prickles that are Brownish-Tan 177C (RHSCC) that are about 0.9 to 1.1 cm. in length.

THE BUD

Size: Large, with a diameter of about 3.0 to 3.3 cm. and a length (depth) of about 4.5 to 5.0 cm.

Form: Ovoid and pointed.

Opening: The buds open slowly.

Color: When the sepals first divide, the color in Spirea Red 63C (RHSCC) at the edge shading lighter to 63D (RHSCC) at the center; when the petals begin to unfurl, the color is more uniformly Spirea Red 63C (RHSCC).

Sepals: The sepals stand up but later curl back as the flower opens.

Color: Inside — Medium Green 146C (RHSCC). Outside — Medium Green 146B (RHSCC).

Calyx:

*Shape.*—Funnel-shaped.

*Size.*—Small, about 1.0 cm. in width and 0.7 cm. in length.

*Aspect.*—Smooth.

*Splitting.*—Calyx does not split.

Peduncle:

*Length.*—About 6 to 7 cm. long.

*Aspect.*—Erect and slender.

*Strength.*—Strong.

*Color.*—Generally Medium Green 146C (RHSCC).

THE FLOWER

Blooming habit: Profuse and continuous from late May or early June to late in the season.

Size: Large, about 9 to 11 cm. in diameter and 4 to 5 cm. in depth.

Borne: Singly and in clusters of usually 5 buds and flowers.

Shape: When bloom first opens, the flowers are cut-shaped but form later becomes flattened to a shallow cup.

Petalage:

*Number of petals.*—30 to 35.

*Arrangement.*—Imbricated.

*Form.*—Round-ovoid.

*Texture.*—Satiny.

*Color.*—Outer petals have a Spirea Red ground 63D (RHSCC) overlaid with Magenta Rose 64D (RHSCC) with Dresden Yellow 5A (RHSCC) at their bases. The inside petals are Magenta Rose 64C (RHSCC), with the reverse sides of the petals being Spirea Red 63B (RHSCC).

Petaloids:

*Number.*—5 to 8.

*Size.*—About 2 to 3 cm. long and about 1 to 2.5 cm. wide.

*Color.*—Magenta Rose 64C (RHSCC).

Persistence: The flower usually shatters after full bloom.

Fragrance: Pleasantly sweet.

Lasting quality: About 5 to 7 days on the plant and about 6 to 8 days as a cut flower. The bloom is not appreciably affected by wet or hot weather.

REPRODUCTIVE ORGANS

Stamens:

*Anthers.*—Numerous, with a length of about 0.4 to 0.6 cm. and in a circular arrangement.

*Filaments.*—The filaments have a length of about 1.2 to 1.4 cm. and a color of Dresden Yellow 5B (RHSCC).

*Pollen.*—The color of the pollen is Light Dresden Yellow 5C (RHSCC).

*Pistils.*—Numerous, with a length of about 1.0 to 1.3 cm.

*Stigmas.*—The color of the stigmas is Light Dresden Yellow 5D (RHSCC).

*Ovaries.*—Ovate with hispid achenes attached to the receptacle wall.

FRUIT

The fruit is fertile and of ovoid shape with a color at maturity of Orange-Red 31A (RHSCC) tinged with Yellow-Green.

This rose plant resembles its seed parent Carefree Beauty (Bucbi) in its floral traits with flowers that resemble those of The Yeoman in form but of a color that is more pink. The plant is notably tolerant of cold winter temperatures without requiring extensive weather protection. Because of that trait and its resistance to foliar diseases such as Blackspot and Powdery Mildew, this plant lends itself for use either as a low-growing everblooming shrub or as a mass-effect low-maintenance bedding plant.

I claim:

1. A new and distinct variety of rose plant substantially as herein shown and described, characterized by its profuse production of large flowers of light red-purple coloration, its vigorous growth habit, its ability to survive without protection under adverse winter conditions, and its resistance to foliar diseases.

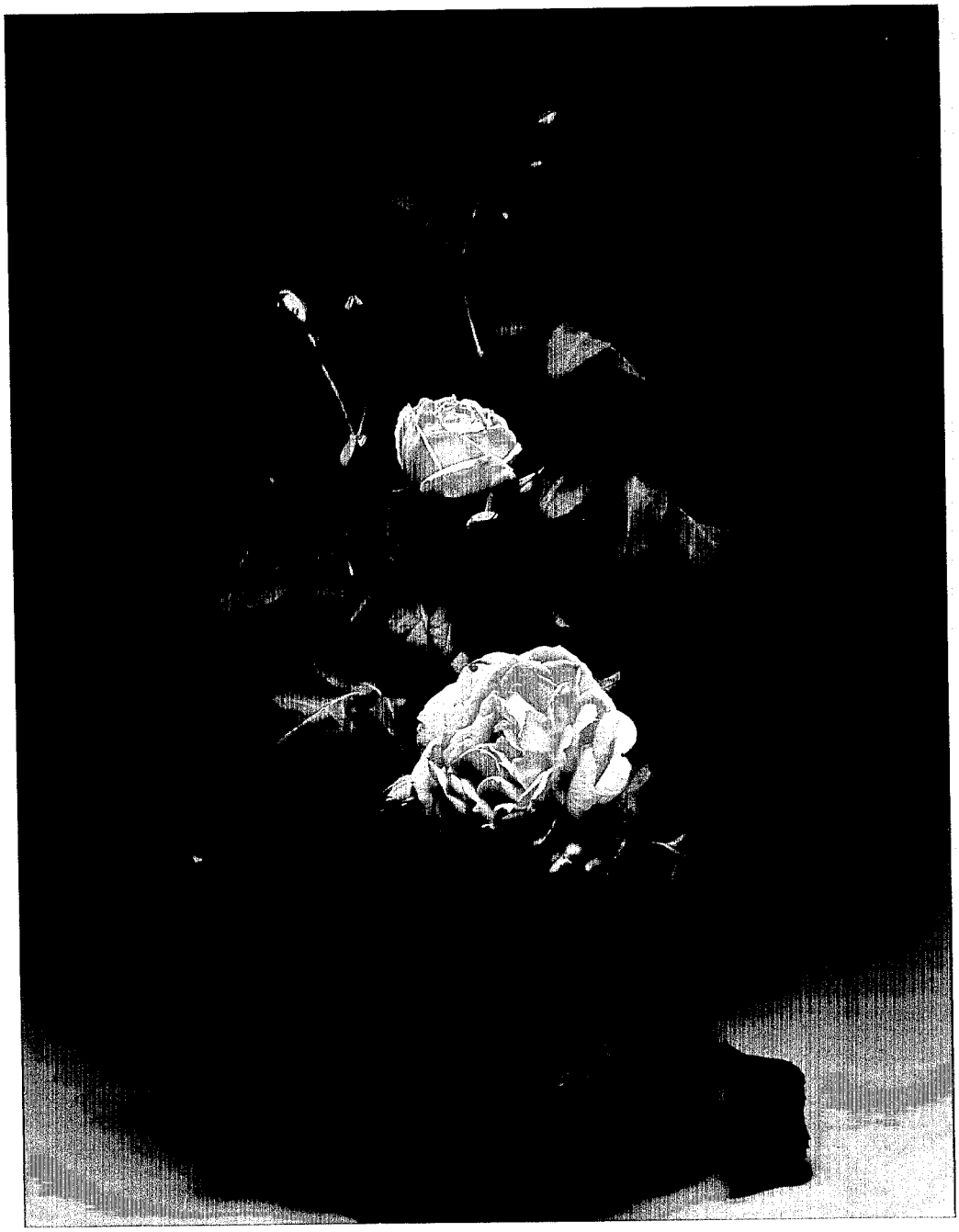

* * * * *